US010219761B2

(12) United States Patent
Li et al.

(10) Patent No.: US 10,219,761 B2
(45) Date of Patent: Mar. 5, 2019

(54) MULTILAYER STAGGERED COUPLING COLLIMATOR, RADIATOR, DETECTOR AND SCANNER

(71) Applicant: Wuhan Acheivision Technology Co., Ltd, Wuhan, Hubei (CN)

(72) Inventors: Yanzhao Li, Hubei (CN); Qingguo Xie, Hubei (CN)

(73) Assignee: WUHAN ACEHIVISION TECHNOLOGY CO., LTD, Wuhan, Hubei (CN)

( * ) Notice: Subject to any disclaimer, the term of this patent is extended or adjusted under 35 U.S.C. 154(b) by 16 days.

(21) Appl. No.: 15/513,796

(22) PCT Filed: Sep. 22, 2015

(86) PCT No.: PCT/CN2015/090250
§ 371 (c)(1),
(2) Date: Mar. 23, 2017

(87) PCT Pub. No.: WO2016/050152
PCT Pub. Date: Apr. 7, 2016

(65) Prior Publication Data

US 2018/0228451 A1 Aug. 16, 2018

(30) Foreign Application Priority Data

Sep. 29, 2014 (CN) .......................... 2014 1 0512964

(51) Int. Cl.
*A61N 5/10* (2006.01)
*A61B 6/03* (2006.01)
(Continued)

(52) U.S. Cl.
CPC ................ *A61B 6/037* (2013.01); *A61B 6/40* (2013.01); *A61B 6/4291* (2013.01); *A61N 5/10* (2013.01); *G21K 1/025* (2013.01)

(58) Field of Classification Search
CPC .... A61N 5/1036; A61N 5/1077; G21K 1/025; A61B 6/037
See application file for complete search history.

(56) References Cited

U.S. PATENT DOCUMENTS 5,231,655 A * 7/1993 Wei ........................ G21K 1/025 378/147
5,293,417 A 3/1994 Wei et al.
(Continued)

FOREIGN PATENT DOCUMENTS

CN 103285526 A 9/2013
CN 103403580 A 11/2013
(Continued)

OTHER PUBLICATIONS

International Search Report dated Nov. 20, 2015 for PCT application No. PCT/CN2015/090250.
(Continued)

*Primary Examiner* — David P Porta
*Assistant Examiner* — Faye Boosalis
(74) *Attorney, Agent, or Firm* — Ohlandt, Greeley, Ruggiero & Perle, LLP

(57) ABSTRACT

A multilayer staggered coupling collimator includes multiple collimating layers, multiple collimating orifices being provided on each collimating layer. At least two collimating layers are in a staggered coupling relationship. Compared with a single-layer collimator, the multilayer staggered coupling collimator can improve the performance, achieve multi-performance selection functions, and have a better machining feasibility. Since the thickness of each collimating layer is less after the collimator is divided into several collimating layers, the machining precision is easy to ensure.

20 Claims, 7 Drawing Sheets

(51) Int. Cl.
*A61B 6/00* (2006.01)
*G21K 1/02* (2006.01)

(56) References Cited

U.S. PATENT DOCUMENTS

| | | | |
|---|---|---|---|
| 6,185,278 B1 | 2/2001 | Appleby et al. | |
| 6,353,227 B1 | 3/2002 | Boxen | |
| 7,386,098 B2 | 6/2008 | Kanack et al. | |
| 2005/0058245 A1 | 3/2005 | Ein-Gal | |
| 2005/0084072 A1* | 4/2005 | Pinchot | G21K 1/02 378/154 |
| 2007/0133749 A1 | 6/2007 | Mazin et al. | |
| 2012/0039446 A1 | 2/2012 | Cui et al. | |
| 2013/0168567 A1 | 7/2013 | Wartski et al. | |

FOREIGN PATENT DOCUMENTS

| | | |
|---|---|---|
| CN | 201092011 U | 1/2015 |
| CN | 204318778 U | 5/2015 |
| CN | 204318776 U | 5/2016 |

OTHER PUBLICATIONS

Chinese Office Action dated Jan. 10, 2018 for Chinese patent application No. 201410512964.4.

* cited by examiner (a) (b) (c)

MULTILAYER STAGGERED COUPLING COLLIMATOR, RADIATOR, DETECTOR AND SCANNER

CROSS-REFERENCED APPLICATIONS

The present application is the national phase of International Application No. PCT/CN2015/090250, entitled "MULTI-LAYER STAGGERED COUPLING COLLIMATOR, RADIATOR, DETECTOR AND SCANNER" filed on Sep. 22, 2015, which claims priority to Chinese Patent Application No. 201410512964.4, titled "MULTI-LAYER STAGGERED COUPLING COLLIMATOR, RADIATOR, DETECTION DEVICE AND SCANNING APPARATUS", filed on Sep. 29, 2014 with the State Intellectual Property Office of People's Republic of China, both of which are incorporated herein by reference in their entireties.

BACKGROUND

1. Field of the Disclosure

The present disclosure relates to the technical field of nuclear medicine imaging, and in particular to a multi-layer staggered coupling collimator, a radiator, a detection device and a scanning apparatus.

2. Discussion of the Background Art

A Single Photon Emission Computed Tomograph (abbreviated as SPECT hereinafter) is an advanced nuclear medicine molecular imaging tool, which can obtain metabolism information on an organism in a noninvasive manner, and play a major role in mechanism study, diagnosis and treatment of critical diseases such as a cardiovascular system disease, a nervous system disease and tumor. The SPECT includes a probe, a rotatable rack, a scanning table, and an image acquisition and processing workstation, where the probe generally includes a scintillator detector and a collimator. In imaging, drugs with radioactive nuclides such as Tc-99m are injected into a human body, and the probe is arranged around the human body to acquire gamma rays from different angles so as to obtain two dimensional radioactive intensity distribution maps from different angles. Then, a three dimensional image that reflects radioactive drug distribution of the human body is obtained by image reconstruction.

A spatial resolution, sensitivity and an imaging field of view are three most important performance indexes of the SPECT. The spatial resolution reflects a capability of the SPECT to distinguish details of an object, and improvement of the spatial resolution can increase richness and definition of details of the acquired image. The sensitivity reflects a capability of the SPECT to detect an object with a low activity, and improvement of the sensitivity can reduce an injection amount of the radioactive drug or imaging time. The imaging field of view reflects a range of sizes of objects which can be scanned by the SPECT, and improvement of the SPECT can accelerate or optimize scanning on a big object. Improvement of one or more of the indexes is a foundational direction of development of the SPECT over years.

The performance of the collimator is one of the main factors influencing the performance of the SPECT system. Optimizing the design of the collimator is an important way to improve the performance of the SPECT system. The collimator is generally a square plate in which through-holes are arranged densely. The plate is generally made of a heavy metal such as lead and tungsten or an alloy thereof, which can block gamma photons that do not fly in holes and allow gamma photons flying through the holes. A linear track of flight of gamma photons can be determined based on the direction of the holes on the collimator and positions on the detector radiated by the gamma photons obtained by the scintillator detector. Performances of the collimator are generally also indicated by the spatial resolution, the sensitivity and the field of view and the like, and the performance indexes are determined by geometric parameters (such as a size of the plate, a shape, a size and a deepness of a hole), a material and a machining precision of the collimator. The indexes are in a mutual constraint relation, that is, increase of one index normally results in decrease of another index. Generally, a suitable combination of performances is selected by performing optimization according to an application demand.

Presently, for imaging of a big animal or a person, the resolution and the sensitivity of the SPECT system needs to be improved greatly. Compared with a positron emission computed tomography which is also a nuclear medicine molecular imaging tool, the SPECT system has a lower resolution and an even lower sensitivity by two orders of magnitude. The low sensitivity and resolution limit the capability of the SPECT system (particularly a clinic SPECT system based on a parallel hole collimator) to diagnose diseases early, find and analyze a lesion quantitatively, and reflect details of an object accurately. Therefore, designing a high performance collimator is still effective means to improve the performances of the SPECT system.

In actual imaging with the clinic SPECT, collimators with different performances may be selected according to application conditions. For this reason, it needs to dismount an old collimator and install a new collimator. Since the collimator is big and heavy, it is not convenient to replace the collimator, and damages may occur during the replacing process. In addition, an SPECT system is normally configured with a very small number of collimators with different performances, and therefore a range of selection is small, which means there may not be sufficient options of collimators to be selected for different applications. An ideal solution to this problem is to design a multiple-performance collimator having adjustable performances.

Processing difficulty is also a main factor to be considered in designing the collimator, and a collimator with an extreme performance or a collimator with complex functions may be impossible due to processing difficulty. Therefore, it needs to consider processing difficulty of the collimator when designing the collimator, in addition to functions of the collimator.

Therefore, it is desired to provide a multi-layer staggered coupling collimator with an improved structure, a radiator, a detection device and a scanning apparatus, so as to solve the problems in the conventional technology.

SUMMARY

In view of above, an object of the present disclosure is to provide a multi-layer staggered coupling collimator, a radiator, a detecting device and a scanning apparatus, to improve one or more performance indexes of the collimator, or support multiple performance combinations to be adjusted or selected.

In order to achieve the above object, the following technical solutions are provided according to the present disclosure.

A multi-layer staggered coupling collimator is provided, which includes multiple collimation layers, where multiple collimation holes are provided on each of the multiple collimation layers and at least two of the multiple collimation layers are coupled to each other in a staggered manner.

A radiator is provided, which includes a radiation source and the multi-layer staggered coupling collimator described above, and the multi-layer staggered coupling collimator is configured to collimate rays emitted by the radiation source.

A detection device is provided, which includes a detector and the multi-layer staggered coupling collimator described above, and the multi-layer staggered coupling collimator is configured to collimate rays, where the collimated rays are applied to the detector.

A scanning apparatus is provided, which includes a detection device and a rack, where the detection device is installed on the rack, the detection device includes the multi-layer staggered coupling collimator described above, and the multi-layer staggered coupling collimator is configured to collimate rays.

It can be seen from the above technical solutions that, compared with a single layer collimator, the multi-layer staggered coupling collimator according to the present disclosure not only has improved performances and multiple selectable performances, but also has good machinability. Since the collimator includes multiple collimation layers, each of the multiple collimation layers is thin, which ensures machining precision.

DETAILED DESCRIPTION OF THE PREFERRED EMBODIMENTS

Before the present disclosure is introduced in detail, concepts of "a collimation layer" and "staggered coupling" are defined first. The collimation layer may be understood from the following two aspects. In a first aspect, the collimation layer may be regarded as a sub-collimator obtained by dividing a collimator (shortening a hole). In a second aspect, the collimation layer may be regarded as one of multiple collimators forming a collimation system by superimposing in series. When a gamma photon passes through a collimator including multiple collimation layers, the gamma photon needs to pass through all collimation layers in sequence. The "staggered coupling" means that center lines of corresponding collimation holes of two collimation layers are not aligned when the two collimation layers are coupled in series. In contrast, alignment coupling means that center lines of corresponding collimation holes of two collimation layers are aligned.

According to the present disclosure, a multi-layer staggered coupling collimator, a radiator, a detection device and a scanning apparatus are provided, which can improve one or more performance indexes of the collimator or can support multiple performance combinations to be adjusted or selected.

According to the present disclosure, a radiator is further provided, which includes a radiation source and the multi-layer staggered coupling collimator according to the present disclosure. The multi-layer staggered coupling collimator is configured to collimate rays generated by the radiation source.

According to the present disclosure, a detection device is further provided, which includes a detector and the multi-layer staggered coupling collimator according to the present disclosure. The multi-layer staggered coupling collimator is configured to collimate rays, where the collimated rays are applied to the detector.

According to the present disclosure, a scanning apparatus is further provided, which includes a detection device and a rack, where the detection device is installed on the rack, and the detection device includes the multi-layer staggered coupling collimator according to the present disclosure. The multi-layer staggered coupling collimator is configured to collimate rays.

The multi-layer staggered coupling collimator disclosed in multiple embodiments in the present disclosure is provided in each of the radiator, the detection device and the scanning apparatus disclosed by the present disclosure. Hereinafter a structure of the multi-layer staggered coupling collimator included in the radiator, the detection device and the scanning apparatus is described in detail.

Figure 1:
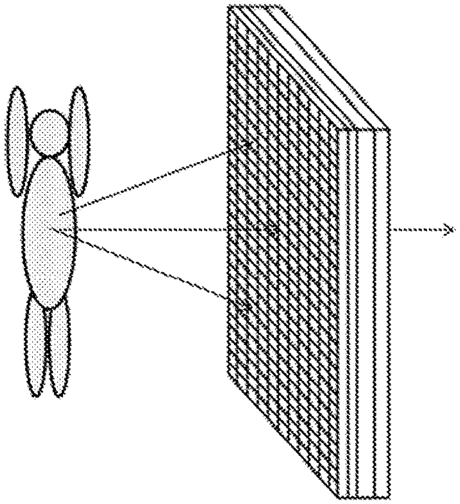
FIG. 1 is a schematic diagram showing that a four-layer collimator collimates gamma rays.
Figure 2:
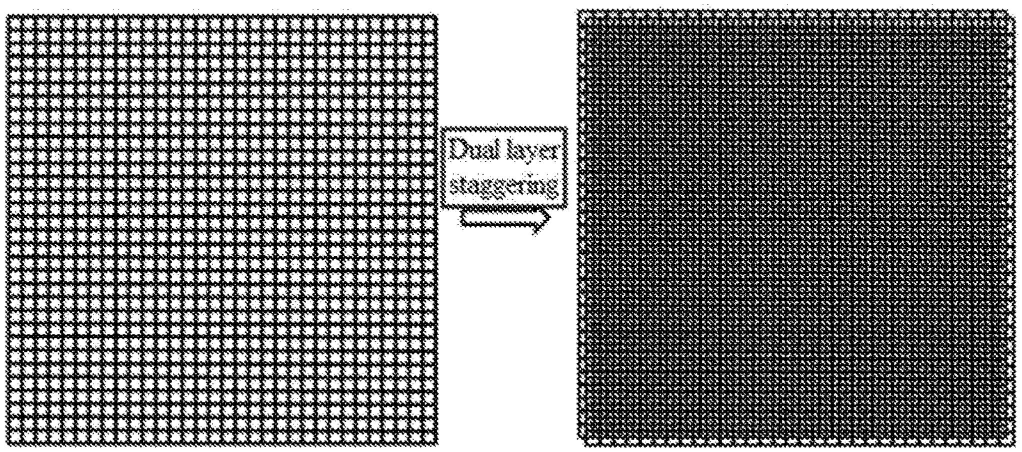
FIG. 2 is a schematic diagram showing comparison of results before and after dual layer staggering in a case that collimation holes in a multi-layer staggered coupling collimator according to the present disclosure have a shape of square.

As shown in FIG. 1 and FIG. 2, the multi-layer staggered coupling collimator includes multiple collimation layers.

Multiple collimation holes are provided on each of the multiple collimation layers. At least two of the multiple collimation layers are coupled to each other in a staggered manner. Collimation holes of the collimation layers may have the same type or different types. Generally the collimation holes have the same type, while the type of the collimation hole is selected according to actual application demands.

The staggered coupling collimator includes three types in the following.

In a first type, positions of all the collimation layers of the staggered coupling collimator are unchangeable. That is, after the collimation layers are staggered, all the collimation layers can not move any more relative to each other. The collimation layer may be fixed by means of screw in a hole punched in the collimation layer, or by means of a housing with a slot. The multi-player staggered coupling collimator of the first type has only one manner of staggering, but performance indexes of the collimator can still be improved.

In a second type, positions of a part of the collimation layers of the staggered coupling collimator are adjustable. That is, after the collimation layers are staggered, the collimation layers may be staggered again according to a new demand. Not all the collimation layers are changeable. Only positions of a part of the collimation layers are changeable to be staggered. The collimator is provided with a guide rail, the part of the changeable collimation layers may be adjusted with the guide rail. The guide rail may have a function of lock catch. Performance indexes of the collimator can be improved after staggering.

In a third type, positions of all the collimation layers of the staggered coupling collimator are adjustable. That is, after the collimation layers are staggered, the collimation layers may be staggered again according to a new demand. Any of the collimation layers may be selected to be staggered as needed. The adjustable collimation layers may be adjusted with a guide rail as in the second type. The guide rail may have a function of lock latch. Performance indexes of the collimator can be improved after staggering.

The multi-layer staggered coupling collimator provided according to the present disclosure has two features: firstly, gamma beams are collimated by at least two collimation layers in the collimator, and secondly, at least two collimation layers are coupled to each other in a staggered manner. The second feature includes two configurations: firstly, all adjacent collimation layers are coupled to each other in a staggered manner; and secondly, not all adjacent collimation layers are coupled to each other in a staggered manner. The second configuration is mainly applied to a case of a large number of collimation layers. For example, a first layer and a second layer are aligned and not staggered, while the first layer and a third layer are staggered. Apparently, since the first layer and the second layer are aligned, the second layer and third layer are staggered.

In a case that the collimator includes multiple collimation layers, thicknesses of the multiple collimation layers may be different, or may be the same. A thickness of each layer may be determined according to an actual demand. In a case that the thicknesses of the collimation layers are different, a ratio of a minimum thickness to a maximum thickness ranges from 1:1 to 1:11.

An effective aperture size and even a shape of the collimation holes in a case of staggered coupling are different from that in a case of alignment coupling, resulting in different performances between the staggered coupling collimator and the alignment coupling collimator (equivalent to a single layer collimator). Further, an internal structure and a performance of the multi-layer staggered coupling collimator are changed as a staggering direction, a staggering amount, the number of layers of the collimator or a layer thickness is changed. Based on this principle, with the multi-layer staggered coupling collimator according to the present disclosure, a high performance collimator can be implemented in which at least one of a spatial resolution and sensitivity is improved (compared with a single layer collimator equivalent to a collimator for which all layers are coupled to each other in an alignment manner), and a performance adjustable collimator can be implemented in which one or more of parameters such as a staggering direction for the layers, a staggering amount for the layers, the number of layers, a thickness of the layers are adjustable.

The multi-layer staggered coupling collimator according to the present disclosure may include N collimation layers coupled in a staggered manner, where a value of N may range from 2 to 30, or may be greater than 30. The value of N is selected according to an actual application demand, in combination with the number and thickness of layers, assembling ability of the collimator and the like. At least two collimation layers among the N collimation layers are coupled in a staggered manner. Practically, it may be the case that all adjacent collimation layers are coupled in a staggered manner. In this case, a position of the first layer may be the same as a position of the third layer.

Figure 8:
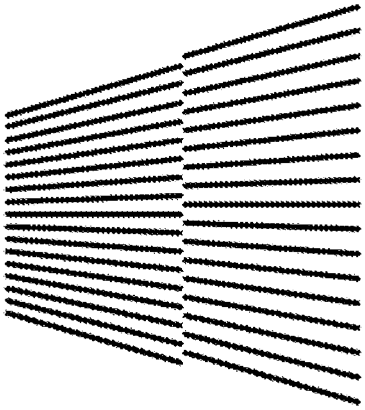
FIG. 8 is a schematic diagram of a convergent dual layer staggered coupling collimator.

Optional collimation layer types include a type of parallel hole collimator, a type of divergent collimator and a type of convergent collimator. Different collimation layer types have different structure features, different performances, and different applications. The parallel hole collimator has the features that all through-holes are parallel, such that an object's image has the same size as the object. This collimator is most commonly used in a clinical SPECT requiring an equal sensibility and resolution in a large field of view. The divergent collimator has the features that holes arranged densely on the collimator are not parallel, such that a pitch of holes becomes larger from a gamma camera end to an object end, so as to generate a shrunken image of the object. This collimator may be applied to a system for imaging a large object with a small detector. The convergent collimator has the reverse feature to the divergent collimator, that a pitch of holes becomes smaller from a gamma camera end to an object end, so as to generate an amplified image of the object. This collimator is generally applied to a local imaging application requiring a high resolution and high sensitivity in a small field of view. A pinhole collimator has the feature that only one small hole is used to generate an inverted image of an object based on a pinhole imaging principle. This collimator is generally applied to a SPECT system requiring a high resolution in a small field of view, and is commonly used in animal imaging. Reference is made to FIG. 8, which is a schematic diagram of a convergent dual layer staggered coupling collimator. A detector is placed on a right side of the collimator, i.e., a right side of FIG. 8. The collimator is convergent in relative to the detector. In a case that rays are emitted from a left side to a right side, the collimator is convergent; and in a case that rays are emitted from the right side to the left side, the collimator is divergent. Convergence or divergence is defined in relative to the detector.

Types and staggering design of collimation holes of the multi-layer staggered coupling collimator according to the present disclosure include but not limited to the following five designs.

In a first design, as shown in FIG. 2, the collimator has the following features. Collimation holes on the collimation layers have a shape of square (for a clear description, it is assumed that a direction of one group of opposite sides of the square is y direction and a direction of the other group of opposite sides is z direction). The collimation holes are arranged in a square grid (arranged in the y direction and the z direction); all adjacent collimation layers among the N collimation layers are staggered in only the y direction, in only the z direction, or in both the y direction and the z direction. The collimation layers are staggered such that a pitch of holes of a squared pattern obtained by projecting the collimator in a direction parallel to the hole direction is ½ to 1/M of a pitch of holes on the collimation layers, where a value of M ranges from 2 to N.

Figure 3:
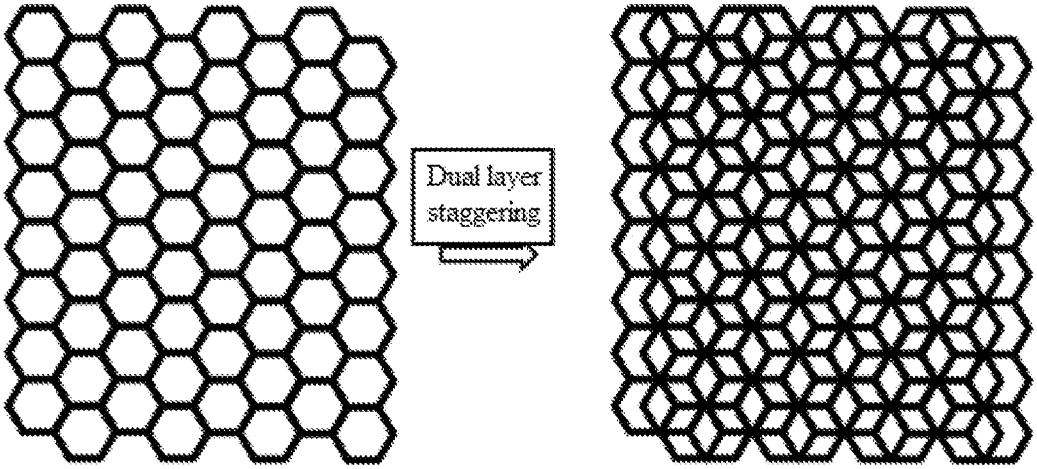
FIG. 3 is a schematic diagram showing comparison of results before and after dual layer staggering in a case that collimation holes in a multi-layer staggered coupling collimator according to the present disclosure have a shape of regular hexagon.
Figure 4:
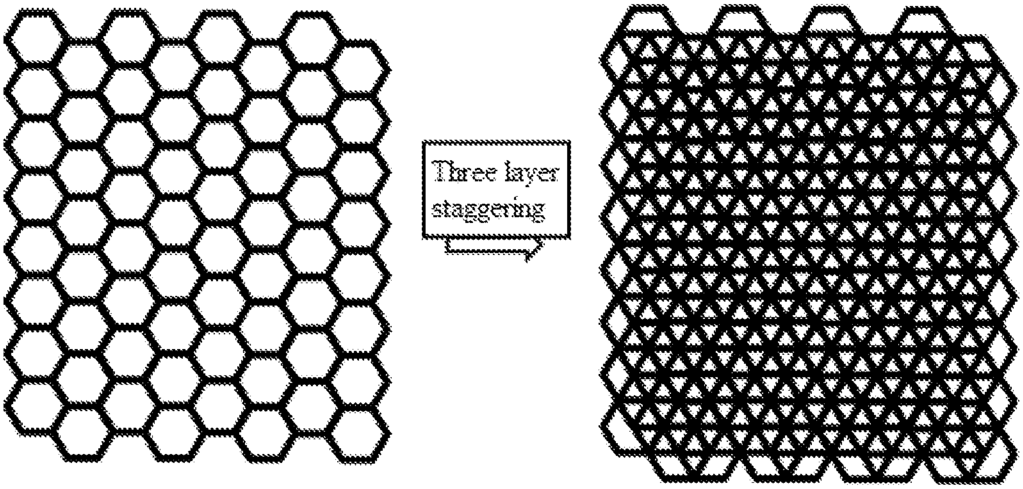
FIG. 4 is a schematic diagram showing comparison of results before and after three layer staggering in a case that collimation holes in a multi-layer staggered coupling collimator according to the present disclosure have a shape of regular hexagon.

In a second design, as shown in FIG. 3 and FIG. 4, the collimator has the following features. Collimation holes on a collimation layer have a shape of regular hexagon, and the regular hexagon holes are arranged in a regular triangular grid (each grid unit has a shape of regular triangular, and each grid point corresponds to a center of a collimation hole). All adjacent collimation layers among the N collimation layers are staggered with each other. In the staggered collimation layers, a center of a collimation hole on a collimation layer is aligned with a common vertex of adjacent hexagon holes of an adjacent collimation layer (distances between the common vertex and centers of three adjacent holes are the same).

Figure 6:
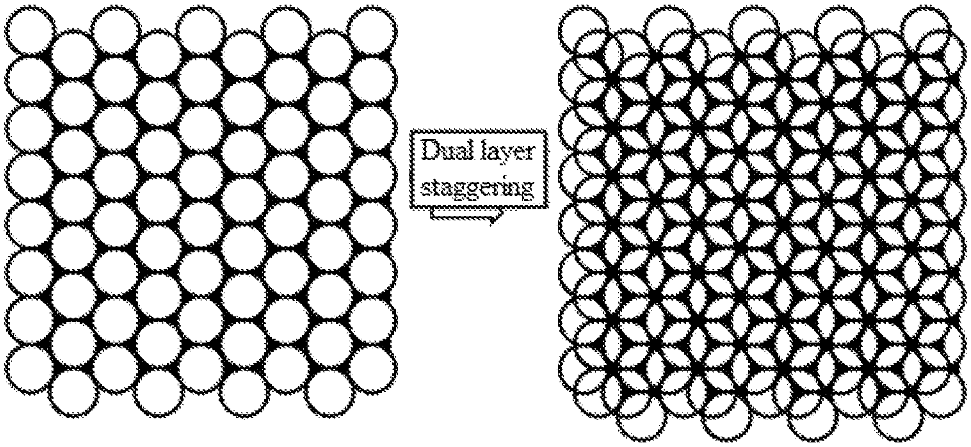
FIG. 6 is a schematic diagram showing comparison of results before and after dual layer staggering in a case that collimation holes in a multi-layer staggered coupling collimator according to the present disclosure have a shape of round.

In a third design, as shown in FIG. 6, the collimator has the following features. Collimation holes on a collimation layer have a shape of round or any polygon approximate to round. The holes with the shape of round or any polygon approximate to round are arranged in a regular triangular grid. All adjacent collimation layers among the N collimation layers are staggered with each other. In the staggered collimation layers, a center of a hole on a collimation layer is aligned with a point on an adjacent collimation layer (the point is located in a region surrounded by three holes which are adjacent to each other, and distances between the point and centers of the three holes are the same).

In a fourth design, as shown in FIG. 6, the collimator has the following features. Collimation holes on a collimation layer have a shape of round or any polygon approximate to round, and the collimation holes are arranged in a square gird (each grid unit is square, and each grid point in the grid corresponds to a center of a collimation hole); and all adjacent collimation layers among the N collimation layers are staggered. Assuming that a direction of one group of opposite sides of the square is y direction and a direction of the other group of opposite sides is z direction, the collimation layers are staggered in the y direction and/or z direction, i.e., in a direction of only one group of parallel sides of the square grid or in both directions of the two group of parallel sides of the square grid. The staggering amount is ½ of a pitch of holes.

Figure 5:
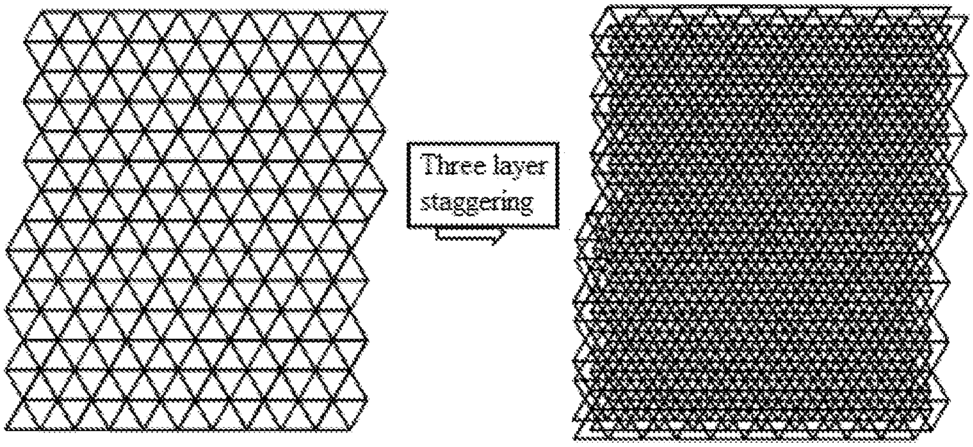
FIG. 5 is a schematic diagram showing comparison of results before and after three layer staggering in a case that collimation holes in a multi-layer staggered coupling collimator according to the present disclosure have a shape of regular triangle.

In a fifth design, as shown in FIG. 5, the collimator has the following features. Collimation holes on a collimation layer have a shape of regular triangle, and the collimation holes are arranged in a regular hexagon grid (each grid unit is a regular hexagon, and each grid point in the grid corresponds to a center of a collimation hole). All adjacent collimation layers among the N collimation layers are staggered. The collimation layers are staggered in a direction of one side of a triangular hole by a staggering amount of sqrt(3)/2 times of a side length of a regular hexagon grid unit (sqrt indicates an extraction operation). An approximate value may be assigned to the staggering amount in a case that the staggering amount is an infinite non-circulating decimal or an infinite circulating decimal.

Figure 7:
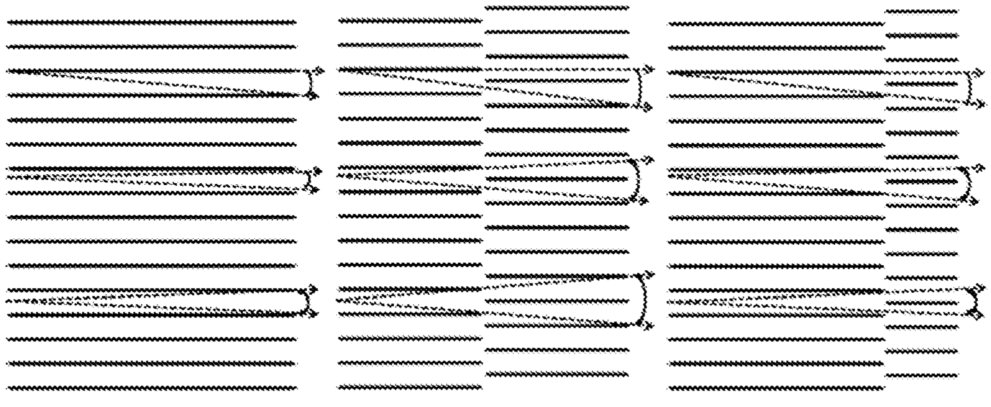
FIG. 7 is a schematic diagram showing two designs for improving sensitivity by using dual layer staggered coupling in a multi-layer staggered coupling collimator according to the present disclosure, where FIG. 7(*a*) is a schematic diagram of a case that there is no staggering, FIG. 7(*b*) is a schematic diagram of a first type of dual layer staggered coupling design, and FIG. 7(*c*) is a schematic diagram of a second type of dual layer staggered coupling design.

As shown in FIG. 7, the collimators in FIG. 7(*a*), FIG. 7(*b*) and FIG. 7(*c*) have the same total thicknesses and the same sizes and pitches of holes on collimation layers, while staggering design is adopted in FIG. 7(*b*) and FIG. 7(*c*), such that thicker beams (indicated by dotted lines and arcs in the figures) can pass, leading to higher sensitivity than the single layer design in FIG. 7(*a*). In FIG. 7(*b*), a ratio of thicknesses of two collimation layers is 1:1, and in FIG. 7(*c*), a ratio of thicknesses of two collimation layers is 3:1. Although the design of two layers is adopted in both FIG. 7(*b*) and FIG. 7(*c*), they have different effect because of the different ratios of thicknesses. In FIG. 7(*b*), a thicker beam from a point source is allowed to pass, leading to higher sensitivity.

Figure 9:
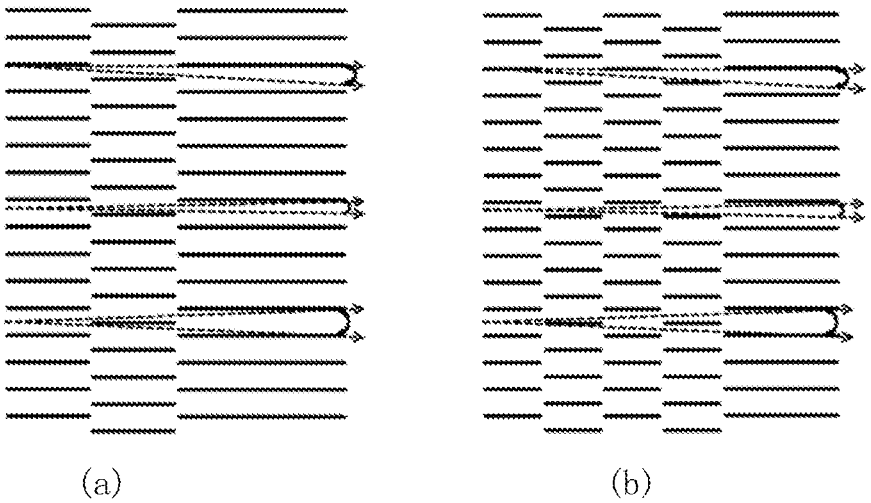
FIG. 9 is a schematic diagram of two designs of a multi-layer staggered coupling collimator with a high resolution, where FIG. 9(*a*) is a schematic diagram of a first design of the multi-layer staggered coupling collimator with a high resolution, and FIG. 9(*b*) is a schematic diagram of a second design of the multi-layer staggered coupling collimator with a high resolution.

As shown in FIG. 9, collimators shown in FIG. 9(*a*) and FIG. 9(*b*) have a same total thickness, in which adjacent layers are coupled in a staggered manner. In FIG. 9(*a*), three collimation layers are provided, and a ratio of thicknesses of the three collimation layers is 1:1:2 from left to right. In FIG. 9(*b*), five collimation layers are provided, and a ratio of thicknesses of the five collimation layers is 1:1:1:1:2 from left to right. Both of the two designs have a higher resolution than the single layer design. Because of the different numbers of layers, a higher resolution can be obtained in FIG. 9(*b*) than in FIG. 9(*a*).

Figure 10:
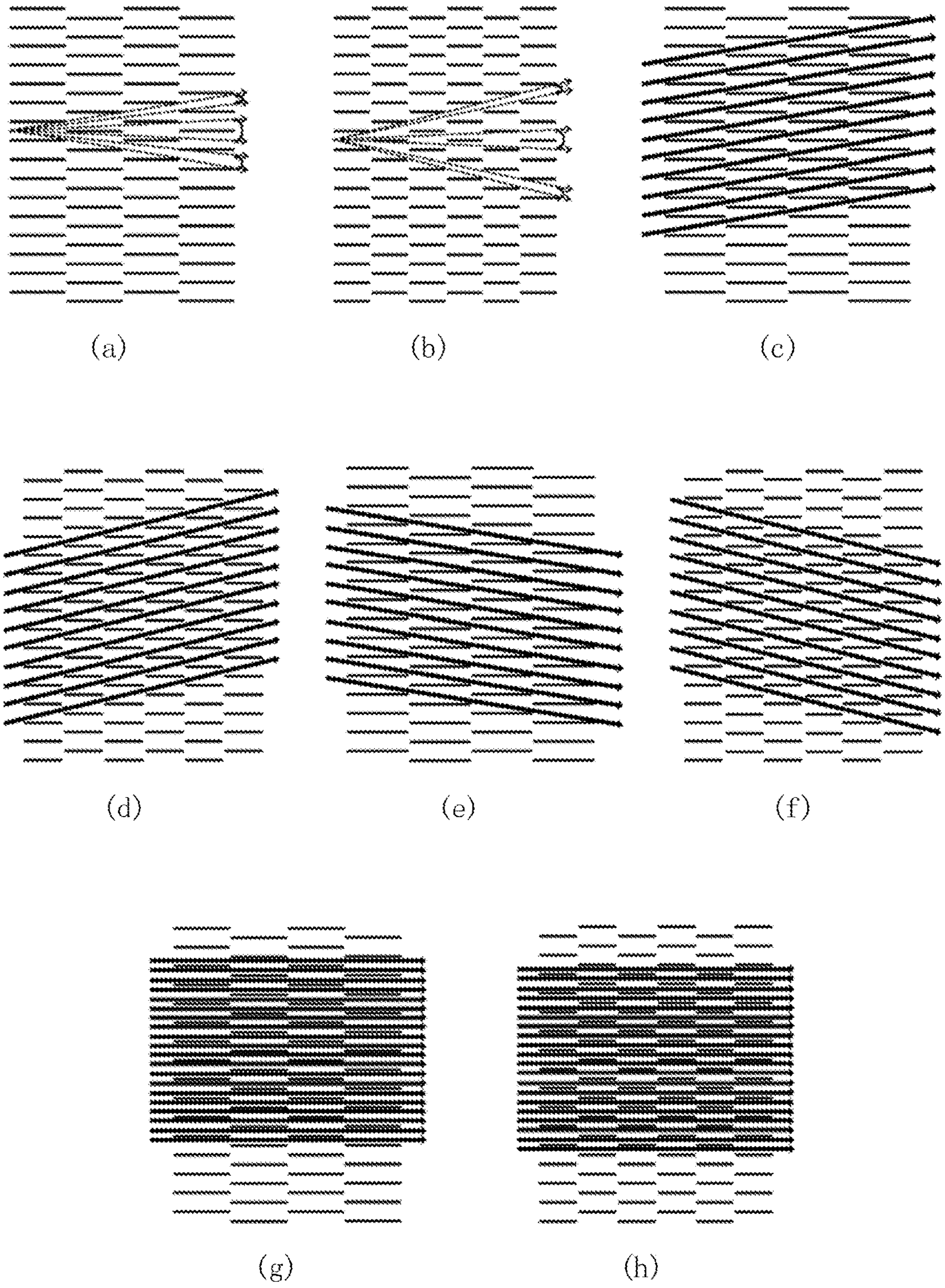
FIG. 10 is a schematic diagram showing different designs of multi-layer staggered coupling collimators for multiple types of parallel beams, where FIGS. 10(*a*) to 10(*h*) are schematic diagrams of different designs respectively.

As shown in FIG. 10, FIG. 10(*a*), FIG. 10(*c*), FIG. 10(*e*) and FIG. 10(*g*) are schematic diagrams of a first design. FIG. 10(*a*) shows three beams (each beam is indicated by dotted-line boundaries and an arc) emitted from one point which can pass through a collimator. FIG. 10(*c*) shows first parallel beams which can pass through the collimator (emitting towards lower right). FIG. 10(*e*) shows second parallel beams which can pass through the collimator (emitting in a direction parallel to the holes). FIG. 10(*g*) shows third parallel beams which can pass through the collimator (emitting towards upper right). FIG. 10(*b*), FIG. 10(*d*), FIG. 10(*f*) and FIG. 10(*h*) are schematic diagrams of a second design. FIG. 10(*b*) shows three beams (each beam is indicated by dotted-line boundaries and an arc) emitted from one point which can pass through a collimator. FIG. 10(*d*) shows first parallel beams which can pass through the collimator (emitting towards lower right). FIG. 10(*f*) shows second parallel beams which can pass through the collimator (a direction parallel to the holes). FIG. 10 (*h*) shows third parallel beams which can pass through the collimator (emitting towards upper right). In the two designs, a total thickness of the collimator is the same, the collimation layers have the same thickness, and adjacent layers are staggered. Because of different thicknesses of each collimation layer and different number of layers, an inclination of the first parallel beams and the third parallel beams relative to the direction of holes in the second design is greater than that in the first design, and the beam is thinner in the second design, leading to a better resolution.

Figure 11:
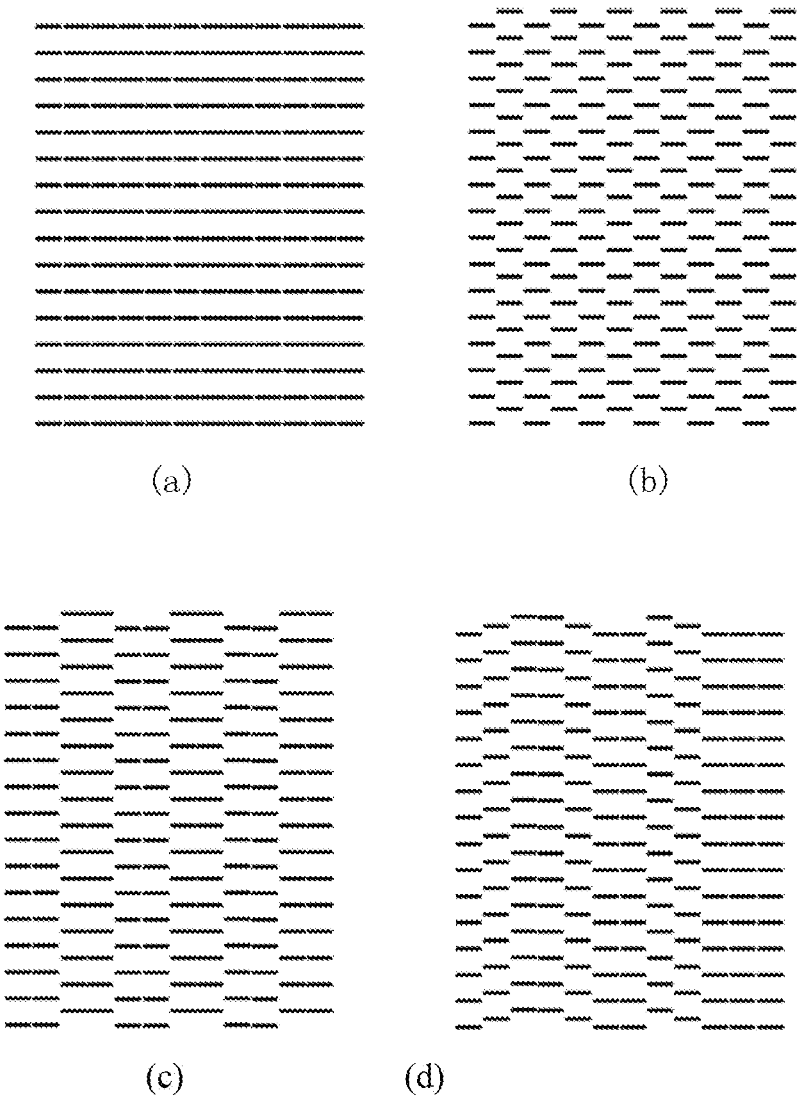
FIG. 11 is a schematic diagram showing several designs of an adjustable collimator, where FIGS. 11(*a*) to 11(*d*) are schematic diagrams of different designs respectively.

As shown in FIG. 11, twelve collimation layers are included in this design. In a case that the twelve collimation layers are aligned, as shown in FIG. 11(*a*), the collimator is equivalent to a single layer design collimator having the same thickness. The results shown in FIG. 11(*b*), FIG. 11(*c*) and FIG. 11(*d*) are obtained by changing the staggering manner. FIG. 11 (*b*) shows a case that all adjacent layers are staggered. FIG. 11(*c*) is equivalent to the design in FIG. 10(*a*). FIG. 11(*d*) shows a more complex adjustment result, in which a staggering amount of adjacent layers is 0 or ⅓ of a pitch of holes. Because of the different staggering, the different designs have different collimation performances to be adapted to different applications. FIG. 11(*a*) only shows one state of the given twelve-layer adjustable collimator.

It can be seen from FIG. 7, FIG. 9 to FIG. 11 that, multiple collimation layers may be staggered in multiple manners. For example, in the staggered multiple collimation layers, odd numbered collimation layers are aligned to each other, and even numbered collimation layers are aligned to each other. For another example, the staggering manner of the multiple collimation layers may be that all adjacent collimation layers are staggered with each other. Alternatively, the multiple collimation layers are grouped into multiple groups in order, and the multiple groups are staggered with each other. The number of collimation layers included in each group may be the same or different. FIG. 11(*b*) shows a case that adjacent collimation layers are staggered. In FIG. 11(*c*), the collimation layers are grouped into six groups, each group includes two collimation layers, and the six groups are staggered with each other. FIG. 11(*d*) shows a relatively complex case of eight groups in total, in which a single collimation layer may also be counted as a group. From left to right, both the third group and the fifth group include two collimation layers, and the eighth group includes three collimation layers. The figures show multiple cases, which are not described respectively herein.

The collimator according to the present disclosure includes Q collimation layers having adjustable coupling relationship, and a value of Q ranges from 2 to 30. Optional collimation layer types may include a type of parallel hole collimator, a type of convergent collimator and a type of divergent collimator. Collimation holes may have a shape of regular triangle, square, regular hexagon, round, polygon approximate to a round, and the like. Based on the type of holes on the collimation layer and the staggering design mentioned above, the collimator may be adjusted into multi-layer staggered collimators with different structures, thereby obtaining collimation results of different performances. In addition, a part of the adjustable collimation layers may be aligned to combine adjacent layers into one layer, or all of the adjustable collimation layers may be aligned to combine the Q layers into one layer.

Compared with the single layer collimator, the multi-layer staggered coupling collimator according to the present disclosure not only has improved performances and multiple selectable performances, but also has good machinability. Since the collimator includes multiple collimation layers, each of the multiple collimation layers is thin, which ensures machining precision.

What is claimed is:

1. A multi-layer staggered coupling collimator, comprising a plurality of collimation layers, wherein:

a plurality of collimation holes are provided on each of the plurality of collimation layers; and at least two of the plurality of collimation layers are coupled to each other in a staggered manner;

wherein the plurality of collimation layers do not have the same thickness.

2. The multi-layer staggered coupling collimator according to claim 1, wherein any adjacent ones in the collimation layers are staggered with each other.

3. The multi-layer staggered coupling collimator according to claim 2, wherein in the staggered plurality of collimation layers, the odd numbered collimation layers are aligned to each other, and the even numbered collimation layers are aligned to each other.

4. The multi-layer staggered coupling collimator according to claim 1, wherein the plurality of collimation layers are grouped into a plurality of groups in order, and the plurality of groups are staggered with each other.

5. The multi-layer staggered coupling collimator according to claim 4, wherein the plurality of groups do not have the same number of collimation layers.

6. The multi-layer staggered coupling collimator according to claim 4, wherein the plurality of groups have the same number of collimation layers.

7. The multi-layer staggered coupling collimator according to claim 1, wherein a ratio of a minimum thickness to a maximum thickness of the plurality of collimation layers ranges from 1:1 to 1:11.

8. The multi-layer staggered coupling collimator according to claim 1, wherein positions of all of the plurality of collimation layers are unchangeable.

9. The multi-layer staggered coupling collimator according to claim 8, wherein a fixing hole is provided on each of the collimation layers and the collimation layers are fixed to each other by means of a screw in cooperation with the fixing hole.

10. The multi-layer staggered coupling collimator according to claim 1, wherein a position of at least one of the collimation layers is adjustable.

11. The multi-layer staggered coupling collimator according to claim 10, wherein a guide rail is provided in the collimator, to adjust the position of the collimation layer by means of sliding on the guide rail.

12. The multi-layer staggered coupling collimator according to claim 1, wherein the collimation holes of the plurality of collimation layers have the same type; and the multi-layer staggered coupling collimator have a collimation layer type of parallel hole collimator, convergent collimator or divergent collimator.

13. The multi-layer staggered coupling collimator according to claim 1, wherein the number of the collimation layers ranges from 2 to 30.

14. The multi-layer staggered coupling collimator according to claim 1, wherein the collimation holes on the collimation layers have a shape of square;

the collimation holes are arranged in a y direction and a z direction and arranged in a square grid, where the y direction is a direction of one group of opposite sides of the square and the z direction is a direction of the other group of opposite sides of the square; and the collimation layers are staggered with each other in the y direction and/or the z direction, such that a pitch of holes in a squared pattern obtained by projecting the collimator in a direction parallel to the holes is ½ to 1/M of a pitch of holes in the collimation layers, where a value of M ranges from 2 to N, and N denotes the number of the collimation layers.

15. The multi-layer staggered coupling collimator according to claim 1, wherein the collimation holes on the collimation layers have a shape of regular hexagon;

the regular hexagon holes are arranged in a regular triangular grid; and the collimation layers are staggered such that a center of each of the collimation holes on any one of the collimation layers is aligned with a common vertex of adjacent ones of the regular hexagon holes on an adjacent collimation layer.

16. The multi-layer staggered coupling collimator according to claim 1, wherein the collimation holes on the collimation layers have a shape of round or any polygon approximate to round;

the collimation holes are arranged in a regular triangular grid; and the collimation layers are staggered such that a center of each of the collimation holes on any one of the collimation layers is aligned with a point on an adjacent collimation layer, the point is located in a region surrounded by three adjacent holes, and distances between the point and centers of the adjacent three holes are the same.

17. The multi-layer staggered coupling collimator according to claim 1, wherein the collimation holes on the collimation layers have a shape of round or any polygon approximate to round;

the collimation holes are arranged in a square grid, each grid unit in the grid is a square, and each grid point in the grid corresponds to a center of one of the collimation holes; and the collimation layers are staggered with each other in a y direction and/or a z direction by a staggering amount of ½ of a pitch of holes, where the y direction is a direction of one group of opposite sides of the square and the z direction is a direction of the other group of opposite sides of the square.

18. The multi-layer staggered coupling collimator according to claim 1, wherein the collimation holes on the collimation layers have a shape of regular triangle;

the collimation holes are arranged in a hexagon grid, each grid unit in the grid is a regular hexagon, and each grid point in the grid corresponds to a center of one of the collimation holes;

the collimation layers are staggered in a direction of a side of the triangular hole by a staggering amount of sqrt (3)/2 of a side length of the hexagon grid unit, sqrt indicates an extraction operation; and an approximate value is assigned to the staggering amount in a case that the staggering amount is an infinite non-repeating decimal or an infinite repeating decimal.

19. A radiator, comprising a radiation source, and the multi-layer staggered coupling collimator according to claim 1, configured to collimate rays emitted by the radiation resource.

20. A detection device, comprising a detector, and the multi-layer staggered coupling collimator according to claim 1, configured to collimate rays, where the collimated rays are applied to the detector.

* * * * *